US012734046B2

(12) United States Patent
Blachon et al.

(10) Patent No.: US 12,734,046 B2
(45) Date of Patent: Sep. 15, 2026

(54) METHOD FOR PERFORMING AN ANKLE ARTHROPLASTY

(71) Applicant: EXTREMIS ROBOTICS, Saint-Martin-d'Hères (FR)

(72) Inventors: Anaelle Blachon, Saint-Martin-d'Hères (FR); Stéphane Lavallee, Saint-Martin-d'Hères (FR)

(73) Assignee: EXTREMIS ROBOTICS, Saint-Martin-d'Hères (FR)

( * ) Notice: Subject to any disclaimer, the term of this patent is extended or adjusted under 35 U.S.C. 154(b) by 621 days.

(21) Appl. No.: 18/210,893

(22) Filed: Jun. 16, 2023

(65) Prior Publication Data

US 2024/0415671 A1 Dec. 19, 2024

(51) Int. Cl.

| | |
|---|---|
| ***A61F 2/46*** | (2006.01) |
| ***A61B 5/11*** | (2006.01) |
| ***A61B 17/16*** | (2006.01) |
| ***A61B 17/88*** | (2006.01) |
| ***A61B 34/10*** | (2016.01) |
| ***A61F 2/42*** | (2006.01) |
| *A61B 34/20* | (2016.01) |
| *A61B 90/00* | (2016.01) |
| *A61F 2/30* | (2006.01) |

(52) U.S. Cl.

CPC ........ *A61F 2/4606* (2013.01); *A61B 17/1642* (2013.01); *A61B 17/1682* (2013.01); *A61F 2/468* (2013.01); *A61F 2/4684* (2013.01); *A61B 2034/102* (2016.02); *A61B 2034/108* (2016.02); *A61B 2034/2051* (2016.02); *A61B 2034/2072* (2016.02); *A61B 2090/364* (2016.02); *A61B 2090/3966* (2016.02); *A61F 2002/30943* (2013.01); *A61F 2002/30948* (2013.01); *A61F 2002/3096* (2013.01); *A61F 2002/3097* (2013.01); *A61F 2002/4205* (2013.01); *A61F 2002/4207* (2013.01); *A61F 2002/4632* (2013.01); *A61F 2002/4633* (2013.01)

(58) Field of Classification Search

CPC .................................................... A61F 2/4606

See application file for complete search history.

(56) References Cited

U.S. PATENT DOCUMENTS

2017/0367766 A1* 12/2017 Mahfouz ............... A61B 34/20
2020/0129311 A1 4/2020 Singh et al.

* cited by examiner

*Primary Examiner* — David H Willse

(74) *Attorney, Agent, or Firm* — Thomas | Horstemeyer, LLP

(57) ABSTRACT

Method for performing an ankle arthroplasty comprising:

fixing the talar tracker, the tibial tracker and the surgical tool tracker, to determine relative poses of the talus, the tibia and the surgical tool with respect to one another, obtaining at least one segmented pre-operative 3D image of the ankle, obtaining at least one per-operative 2D image of the ankle, registering the segmented pre-operative 3D image on each per-operative 2D image, determining an optimized pose of the final tibial component, and an optimized pose of the final talar component, determining a targeted shape of the talus and a targeted shape of the tibia, machining the talus and the tibia, and implanting the final tibial component.

20 Claims, 12 Drawing Sheets

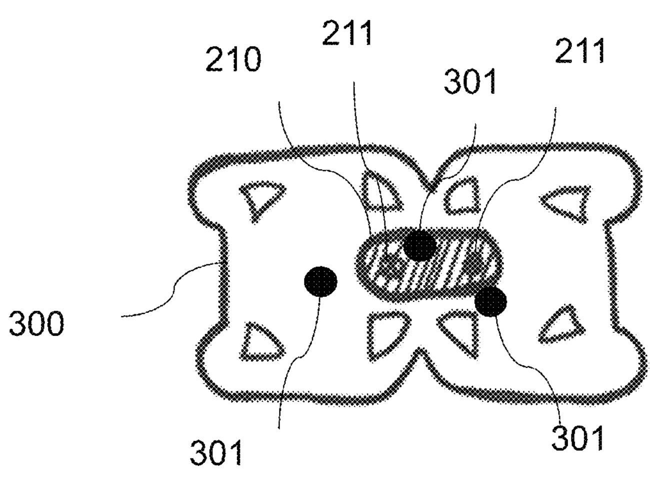
FIGURE 4a
301'
211'
302'
300'
210'
302'
301'
301'
211'
FIGURE 4b
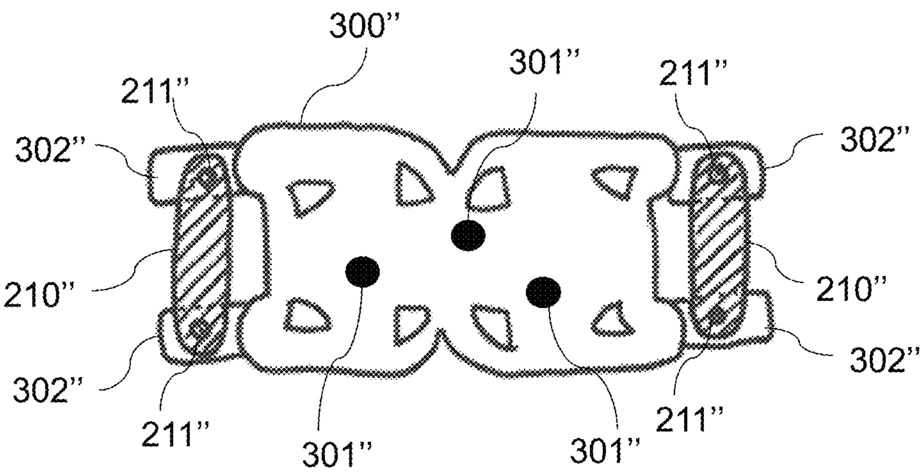
FIGURE 4c

METHOD FOR PERFORMING AN ANKLE ARTHROPLASTY

FIELD OF INVENTION

The present disclosure pertains to the domain of robotic surgeries. Especially, the present disclosure is directed to a method for performing an ankle arthroplasty with a computer-assisted surgery system.

BACKGROUND

Ankle joint replacements, also known as ankle arthroplasties, involve implementing an implant to help a patient recover full motility of his/her ankle. Such implant comprises at least three distinct parts: a talar component, a tibial component and an insert positioned between the talar component and the tibial component and which allows movements of both components with respect to each other and with respect to said insert. To implement those parts, the bones are prepared beforehand. Especially, cuts are realized on the tibia and on the talus to permit fixation of the different components. Obviously, the precision of those cuts is directly related to the correct positioning of the different components of the implant and, consequently, to the level of motility recovered after the surgery. The word “cut” here is employed largely to designate any kind of machining of the concerned bone.

Currently, those surgeries can be performed thanks to at least several different techniques which all lack precision.

A first technique is the oldest one and consists in performing all the cuts manually, the surgeon only relying on his/her experience to both plan the cuts and realized said cuts. Obviously, this first technique is being abandoned as it really lacks precision and imposes to open the ankle largely for the surgeon to correctly see the bones he/she is machining, thus increasing the time of recovery for the patient.

To improve the process, surgical guides have been developed. This kind of guide generally comprises a positioning part thanks to which said guide is attached to the bone and a guiding part adapted to guide a cutting tool such as a sawblade or a burr for instance, while performing the cuts. Unfortunately, the shapes and sizes of the bones vary from one individual to another. Therefore, those surgical guides, in the end, also lack precision. Also, those surgical guides are relatively large and impose to realize quite large incisions in the patient ankle to position them, thus increasing the time of recovery for the patient.

Patient-specific surgical guides, i.e. surgical guides adapted to the particular anatomy of each patient, have thus been developed as well as patient-specific implants. But those patient-specific surgical guides also have several drawbacks. First, their manufacturing is time-consuming as they necessitate to take images of the patient, manually segment the taken images, and then use the segmented images to design and manufacture the corresponding guide. This process can take up to several months, thus delaying the surgery. Second, even if the surgical guide is particularly adapted to fit the patient’s anatomy, the positioning of such surgical guide, before cutting the bones, is realized manually and is thus subjected to human mistakes. Finally, as for the use of generic surgical guides, patient-specific guides impose to realize large incisions in the patient ankle, thus being invasive, and increasing the time of recovery for the patient.

US patent application US2020/0129311 describes a robotic system adapted to perform ankle arthroplasties and a method for verifying the correct positioning of the implant, and especially of the talar component of said implant. This application describes several manual methods to plan the surgery. For instance, a user of the system can position, manually, a virtual implant on a virtual 3D model of the ankle. Alternatively, the user can palpate, with a tracked probe, the borders of the parts to be resected. Then, the application describes a method for verifying the correct positioning of the implant, and especially of the talar component of such implant. Such verification comprises verifying if the current pose of the implant matches the planned pose of said implant. Thus, if the surgical plan, performed manually by the user of the system, lacks precision, the positioning of the implant will also lack precision.

Thus, there remains a need for improving the current technics used to perform ankle arthroplasties.

BRIEF SUMMARY OF THE SUMMARY

The present disclosure aims at solving at least part of the mentioned drawbacks with a method for performing ankle arthroplasty with a computer-assisted surgery system which is more precise than a human hand, and which permits to avoid using a surgical guide, thus permitting to perform the surgery through a smaller incision than the ones currently realized.

An object of the present disclosure thus concerns a method for performing an ankle arthroplasty on a patient’s leg by implanting a final ankle implant comprising at least one final tibial component, at least one final talar component and at least one final insert movable with respect to the final tibial component and to the final talar component, using a computer-assisted surgery system comprising a robotic arm holding a surgical tool and an electromagnetic tracking system comprising at least a talar tracker, a tibial tracker and at least one surgical tool tracker, the method comprising:

- fixing the talar tracker, the tibial tracker and the surgical tool tracker, respectively, to a talus of the patient’s leg, to a tibia of the patient’s leg and to the surgical tool, according to known geometries, to determine relative poses of the talus, the tibia and the surgical tool with respect to one another,
- obtaining at least one segmented pre-operative 3D image of the ankle,
- obtaining at least one per-operative 2D image of the ankle, each per-operative 2D image being acquired while a registration device comprising at least three radiopaque elements and at least one electromagnetic transceiver is placed on the ankle,
- registering the segmented pre-operative 3D image on the per-operative 2D image, using the registration device,
- determining an optimized pose of the final tibial component with respect to the tibia, and an optimized pose of the final talar component with respect to the tibia, based on at least one morphological criterion,
- determining a targeted shape of the talus and a targeted shape of the tibia to permit to position the final tibial component and the final talar component according to their respective planned optimized poses,
- machining the talus and the tibia with the surgical tool held by the robotic arm to obtain the targeted shapes, and
- implanting the final tibial component on the machined tibia, the final talar component on the machined talus, and the final insert of the ankle implant between the final tibial component and the final talar component.

The method can be complemented by one or several of the following features taken alone or in combination.

The method further comprises before implanting the final tibial component, the final talar component and the final insert:

- implanting a trial ankle implant by implanting a trial tibial component on the machined tibia, a trial talar component on the machined talus, and a trial insert between the trial tibial component and the trial talar component,
- checking if a pose of each trial component complies with the at least one morphological criterion, and
- removing the trial ankle implant.

The method further comprises

- determining that additional machining of at least one of the talus and the tibia is needed if the pose of at least one trial component does not comply with the at least one morphological criterion,
- planning and performing said additional machining with the surgical tool, and implanting the final ankle implant.

The method further comprises the step of checking if the poses of each final component complies with the at least one morphological criterion.

The morphological criterion comprises at least one of the following:

- the final tibial component and the final talar component are included in a volume defined by a longitudinal projection of an anterior surface of the tibia bone,
- implant sizes are maximal,
- implant axes are aligned with bone axes, and
- a gap between the tibia and the talus components of the implant is at least as high than a width of the final insert.

The electromagnetic tracking system comprises at least one data processor and an electromagnetic transmitter adapted to emit an electromagnetic field, each of the tibial tracker, the talar tracker and the surgical tool tracker being an electromagnetic receiver adapted to receive and measure the electromagnetic field, the data processor being adapted to determine a relative pose of the talus, the tibia and the surgical tool, based on the electromagnetic field measured by each electromagnetic receiver and on the known geometric relation between each of the tibial tracker and the tibia, the talar tracker and the tibia and the surgical tool tracker and the surgical tool.

The talar tracker is fixed to a medial surface of the talus.

The electromagnetic transmitter is positioned medially with respect to the tibial and talar trackers.

The surgical tool tracker is rigidly fixed to an extension of the robotic arm, the extension being configured to position the surgical tool tracker medially with respect to the electromagnetic transmitter and to the tibial and talar trackers.

Each pre-operative 3D image(s) is acquired while the patient is in a weight bearing position.

Determining the optimized pose of the final tibial component with respect to the tibia and the optimized pose of the final talar component with respect to the tibia is further based on a set of kinematic data acquired by

- applying defined constraints on the ankle to be treated,
- virtually simulating the applied constraints on the registered 3D image,
- the optimized pose of the final tibial component and of the final talar component being defined to prevent impingement between the final tibial component, the final talar component, the tibia and the talus when the constraints are applied.

The optimized pose of the final tibial component and of the final talar component are defined so that a mobility of the treated ankle is at least as wide before and after implantation of the ankle implant, the mobility of the treated ankle being estimated based on at least one of (i) a maximal angle of possible plantar flexion and a maximal angle of possible dorsal flexion of the treated ankle and (ii) a maximal varus/valgus balance.

The present disclosure also concerns a method for performing an ankle arthroplasty on a patient's leg by implanting a final ankle implant comprising at least one final tibial component, at least one final talar component and at least one final insert movable with respect to the final tibial component and to the final talar component, using a computer-assisted surgery system comprising a robotic arm holding a surgical tool and an electromagnetic tracking system comprising at least a talar tracker, a tibial tracker and at least one surgical tool tracker, the method comprising:

- fixing the talar tracker, the tibial tracker and the surgical tool tracker, respectively, to a talus of the patient's leg, to a tibia of the patient's leg and to the surgical tool, to determine relative poses of the talus, the tibia and the surgical tool with respect to one another,
- obtaining at least one per-operative 3D image of the ankle while a registration device comprising at least three radiopaque elements and at least one electromagnetic transceiver is placed on the ankle, the 3D image being acquired for a given position of the talus with respect to the tibia,
- segmenting the per-operative 3D image of the ankle,
- recording an optimized pose of the final tibial component with respect to the tibia, and an optimized pose of the final talar component with respect to the tibia, based on at least one morphological criterion,
- determining a targeted shape of the talus and a targeted shape of the tibia to permit to position the final tibial component and the final talar component according to their respective planned optimized poses,
- machining the talus and the tibia with the surgical tool held by the robotic arm to obtain the targeted shapes, and
- implanting the final tibial component on the machined tibia, the final talar component on the machined talus, and the final insert of the ankle implant between the final tibial component and the final talar component, The method can be complemented by one or several of the following features taken alone or in combination.

The given position of the talus with respect to the tibia corresponds to a weight bearing position of the patient, and obtaining the per-operative 3D image of the ankle comprises:

- positioning the patient on a board, in a lying position, feet soles of the patient being positioned against a plate perpendicular to the board,
- determining a hip center of the patient's leg,
- applying a mechanical pressure on the ankle of the patient, along a direction perpendicular to the plate and passing through the hip center, to simulate a weight bearing condition, and
- recording the relative poses of the tibia and the talus with respect to one another in the simulated weight bearing position of the patient.

The relative poses of the tibia and the talus with respect to one another in the simulated weight bearing position of the patient are recorded based on positional data obtained by the electromagnetic tracking system.

The board comprises at least one laser source adapted to emit a laser beam, the method further comprising:

orienting the laser source to propagate the laser beam perpendicularly to the plate and toward the hip center, the direction of the application of the mechanical pressure being materialized by said laser beam.

The mechanical pressure depends on at least a weight of the patient.

The mechanical pressure is modified by displacing, manually or automatically, the plate.

Determining the optimized pose of the final tibial component with respect to the tibia and the optimized pose of the final talar component with respect to the tibia, is further based on a set of kinematic data acquired by applying defined constraints on the ankle to be treated, and virtually simulating the applied constraints on the registered 3D image, the optimized pose of the final tibial component and of the final talar component being defined to prevent impingement between the final tibial component, the final talar component, the tibia and the talus when the constraints are applied.

The optimized pose of the final tibial component and of the final talar component are defined so that a mobility of the treated ankle is at least as wide before implantation of the ankle implant, the mobility of the treated ankle being estimated based on at least one of (i) a maximal angle of possible plantar flexion and a maximal angle of possible dorsal flexion of the treated ankle and (ii) a maximal varus/valgus balance.

BRIEF DESCRIPTION OF THE DRAWINGS

Further details and advantages are described hereunder in relation with the accompanying drawings.

FIGS. 4*a*, 4*b*, 4*c* respectively illustrate a cooperation between the registration device of FIG. 4 and an electromagnetic transmitter of the electromagnetic tracking system according to three different embodiments;

DETAILED DESCRIPTION OF THE INVENTION

Figure 1:
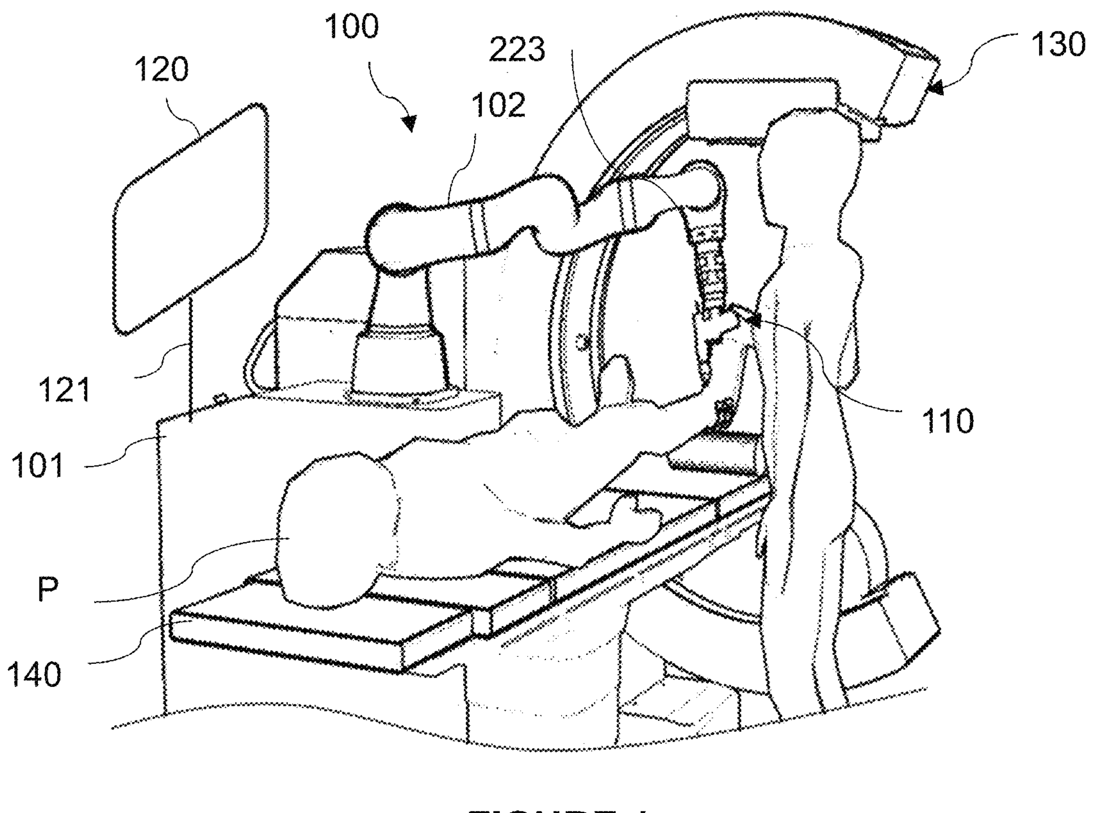
FIG. 1 is a general view of a computer-assisted surgery system adapted to be used to perform an ankle arthroplasty on a patient's leg.

Referring to FIG. 1, a computer-assisted surgery system 100 is illustrated. Such system 100 is particularly adapted to perform an ankle arthroplasty on a patient P and it comprises a base 101 from which extends a robotic arm 102 with motorized joints and which is holding a surgical tool 110, the robotic arm 102 being adapted to allow displacements of the surgical tool 110 according to at least six degrees of freedom. Advantageously, the robotic arm 102 can further be adapted to permit displacements of the surgical tool 110 along at least one redundant degree of freedom, i.e., a total of at least seven degrees of freedom. The surgical tool 110 is, advantageously, removably held by the robotic arm 102 and it can be changed. For instance, the computer-assisted surgery system 100 can comprise at least one input device—not shown—and at least one processing unit adapted to receive inputs transmitted by the user through the input device and to compute instructions to be sent to motorized joints of the robotic arm so as to displace the surgical tool as commanded by the user, but with safety parameter—not detailed in this document—considered by said processing unit. For instance, the input device can be formed as a joystick or a handle mounted on the robotic arm, near the surgical tool 110.

The processing unit can, for instance, comprise one or more microprocessors, one or more random access memories (RAM) and/or one or more read-only memories (ROM), one or more calculators, one or more computers and/or one or more computer programs. The computer program(s) comprise code instructions to compute the needed instructions to be sent to the motorized joints of the robotic arm. In addition, the processing unit may include other devices and circuitry for performing the functions described herein such as, for example, a hard drive, input/output circuitry, and the like. The input/output circuitry can be adapted to treat digital and/or analog signals.

The computer-assisted surgery system 100 can be associated with an electromagnetic tracking system. Such an electromagnetic tracking system 200 is for instance illustrated on FIGS. 2 to 4. We are now going to describe the electromagnetic tracking system 200 illustrated on FIGS. 2 and 3 which both illustrate the ankle to be treated together with the surgical tool 110 held by the robotic arm 102, FIG. 2 illustrating a side view of the set-up and FIG. 3 illustrating a front view of said set-up.

According to the illustrated embodiment, the electromagnetic tracking system 200 comprises several electromagnetic transceivers, among which at least one electromagnetic transmitter 210 adapted to emit at least one electromagnetic field and at least three electromagnetic receivers 220 adapted to receive and measure the emitted electromagnetic field. The electromagnetic tracking system 200 further comprises at least one data processor 230—only schematically represented on FIGS. 2 and 4—adapted to determine the relative poses of each electromagnetic receiver 220 with respect to the electromagnetic transmitter 210 and to determine the relative poses of the objects to which those electromagnetic receivers 220 are attached with respect to one another based on the received and measured electromagnetic field, on a known geometry between said electromagnetic receivers 220 and the tracked objects and on a known pose of the electromagnetic transmitter 210. The three electromagnetic receivers comprise at least two bone trackers, namely a talar tracker and a tibial tracker, and at least one surgical tool tracker. Thus, a first electromagnetic receiver forms the talar tracker 221 attached to a talus Ta of the patient, a second electromagnetic receiver forms the tibial tracker 222 attached to a tibia Ti of the patient and a third electromagnetic receiver forms the surgical tool tracker 223 attached to the surgical tool 110. In the present document, the relative poses determined by the electromagnetic tracking system 200 can be referred to as "positional data". Advantageously, using an electromagnetic tracking system permit to reduce the size and weight of the bone trackers. For instance, each bone tracker can be formed as a cube with edges smaller than 10 mm and weighing less than 10 g. Such dimension and weight ensure that the bone trackers do not interfere with any movement of the ankle potentially needed during the surgery. As any tracking system, the electromagnetic tracking system is configured to determine, at a predetermined frequency, the relative pose of the transceivers with respect to one another. The predetermined frequency is advantageously greater than 100 Hz.

Figure 2:
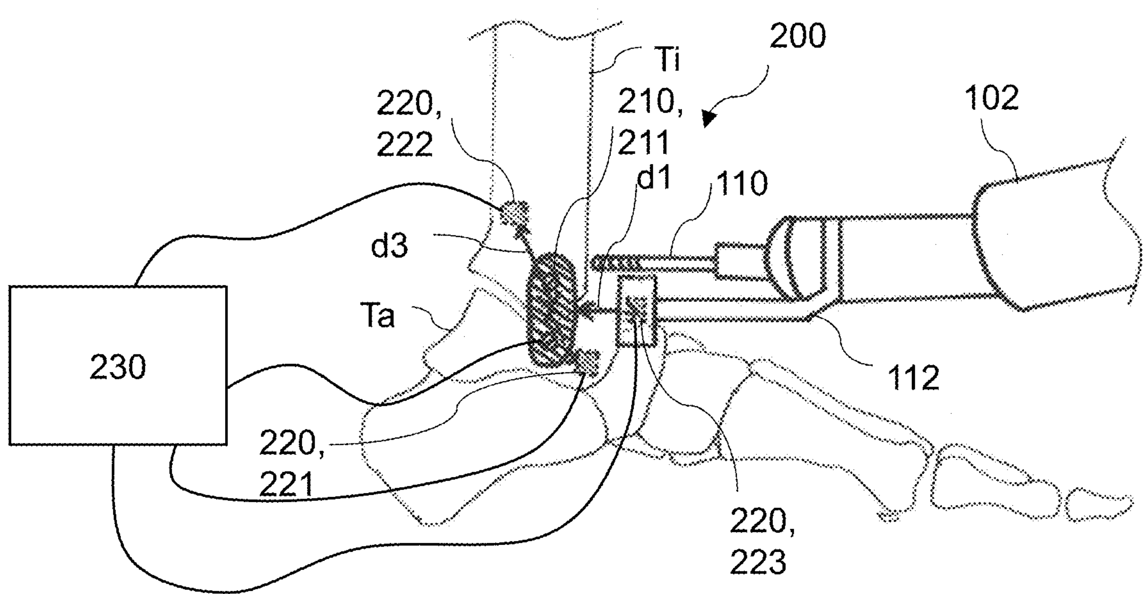
FIG. 2 is a side view of an ankle to be treated, equipped with an electromagnetic tracking system and illustrated together with a surgical tool held by a robotic arm of the computer-assisted surgery system illustrated on FIG. 1.
Figure 3:
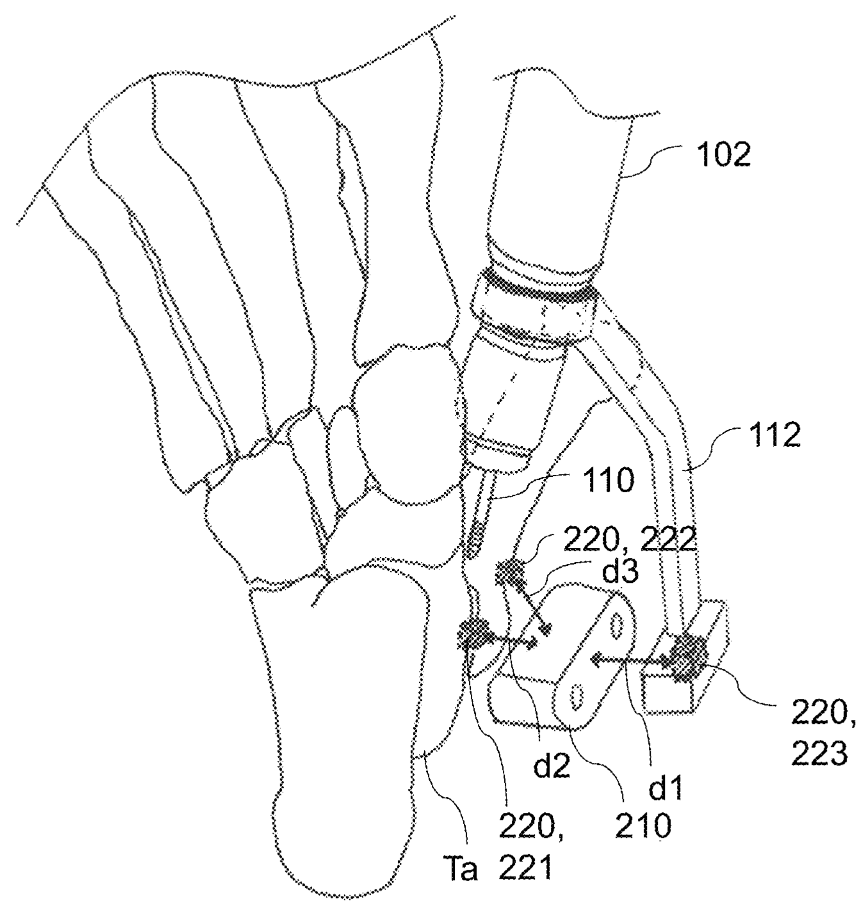
FIG. 3 is a front view of an ankle to be treated, equipped with an electromagnetic tracking system and illustrated together with a surgical tool held by a robotic arm of the computer-assisted surgery system illustrated on FIG. 1.

As illustrated on FIGS. 2 and 3, the robotic arm 102 can advantageously comprise an extension 112 to which the third electromagnetic receiver 223 is attached. This extension 112 has a fixed and known geometry with respect to the surgical tool 110, so that the data processor 230 of the tracking system can compute the pose of the surgical tool 110 based on the determined pose of said third electromagnetic receiver 223. The geometry of this extension 112 is configured so that any distance d1, d2, d3 measured between the electromagnetic transmitter 210 and any of the electromagnetic receivers 220 is lower than 60 mm, advantageously lower than 50 mm. Also, this extension 112 ensures that the surgical tool tracker 223 is at a distance sufficient from the metallic parts of the surgical tool 110 which could disturb the transmitted electromagnetic field, and thus result in an erroneous localization of the tracked objects.

The electromagnetic transmitter 210 comprises at least a transmitting part comprising of one or more transmitting coils rigidly linked to each other. This electromagnetic transmitter 210 can be placed directly on a surgical table on which the patient lies, or it can be included in a leg-holder adapted to support the ankle to be treated during the surgery. The electromagnetic receivers 220 respectively comprise an anchoring part adapted to be fixed to the tracked objects, such as the bones of the patient or the surgical tool, and a receiving part comprising one or more receiving coils rigidly linked to each other. Consequently, the respective pose of the objects linked to each of the electromagnetic receivers can be determined as long as the geometry of the links between said electromagnetic transmitter and the objects to be tracked are known. Typically, the electromagnetic transmitter comprises three coils and each electromagnetic receiver comprises three coils. Therefore, nine measurements can be obtained for each receiver, and the six independent degrees of freedom of the position and orientation of a transform matrix between the concerned receiver reference system and the transmitter reference system can be determined, for instance by least squares optimization method.

As illustrated on FIGS. 2 and 3, the talar and tibial trackers 221, 222 are advantageously attached to a medial surface of the talus and to a medial surface of the tibia, respectively. Especially, the tibial tracker 222 is fixed to the tibia Ti so that a distance measured between a malleolus of such tibia and a point at which the tibial tracker 222 is fixed to the bone is comprised between 4 cm and 6 cm. Positioning the trackers medially, i.e. on the medial surfaces, permits to prevent any unwanted collision between the surgeon and the tracking system, which could impact the precision of the tracking system.

According to a non-illustrated embodiment, the talar and tibial trackers could be attached to lateral surfaces of the respective objects to be tracked. Such a lateral configuration advantageously permits to prevent to hit the non-treated ankle with the extension of the robotic arm to which the surgical tool tracker is attached. Also, if the trackers are attached laterally, a fourth electromagnetic receiver could be used to track a fibula of the treated leg. Using this fourth tracker thus improves the precision of the tracking as the pose of said fibula is otherwise considered fixed with respect to the tibia bone.

Therefore, the electromagnetic tracking system 200 permits to determine, at any time, at least the relative poses of the patient's talus Ta, with respect to the patient's tibia Ti, with respect to the surgical tool 110.

Figure 4:
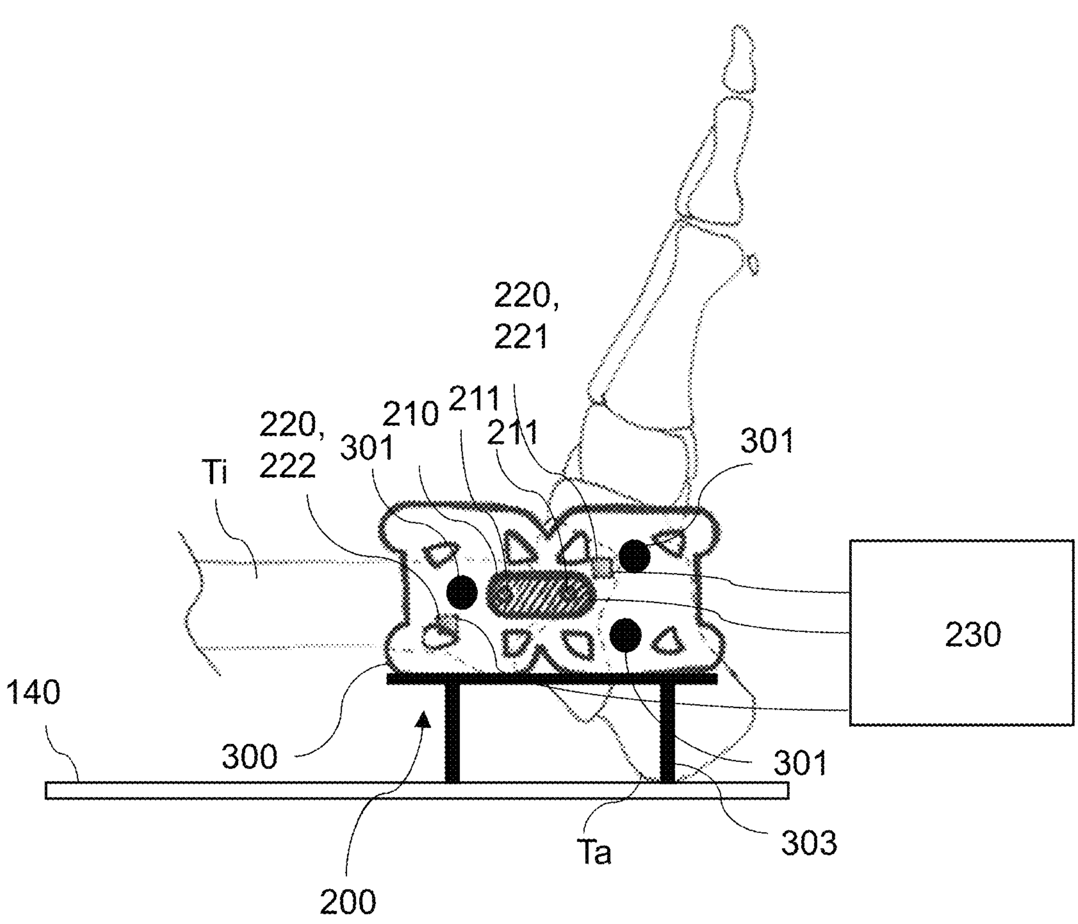
FIG. 4 is a side view of the ankle illustrated on FIG. 2, on which a registration device according to a first embodiment has been attached.

Optionally, the electromagnetic transmitter 210 can comprise an attaching part 211 adapted to receive a registration device 300, according to a first embodiment. FIG. 4 illustrates such a registration device 300 removably attached to the electromagnetic transmitter 210. According to the illustrated embodiment, the attaching part 211 is formed as two pins adapted to be received, respectively, in recesses of complementary shapes formed within the registration device 300.

According to the first embodiment illustrated on FIG. 4, the electromagnetic transmitter 210 is more particularly attached to a center of the registration device 300. FIGS. 4*a*, 4*b*, 4*c* illustrate three distinct embodiments of this registration device 300, 300', 300''. FIG. 4*a* illustrates a first example of the first embodiment which corresponds to the one illustrated on FIG. 4 wherein the electromagnetic transmitter 210 is attached to the center of the registration device 300. According to a second example illustrated on FIG. 4*b*, the electromagnetic transmitter 210' is attached to a side of the registration device 300'. According to a third example illustrated on FIG. 4*c*, the electromagnetic tracking system can comprise two electromagnetic transmitters 210'' respectively attached to each side of the registration device 300''. To allow the attachment of the electromagnetic transmitter 210', 210'' to the sides of the registration device 300', 300'', such registration device 300', 300'' comprises two tabs 302', 302'' on which are formed the recesses adapted to receive the pins of the electromagnetic transmitter. Obviously, this is only an example and the attaching part of the electromagnetic transmitter could be realized according to any other known means for removably attaching two pieces together.

As schematically illustrated, the registration device 300 is arranged on a support 303, itself positioned on the surgical table 140, in the vicinity of the ankle to be treated. Advantageously, this support is positioned so that a distance measured between the electromagnetic transmitter 210 and any of the electromagnetic receivers is smaller than 60 mm, advantageously smaller than 50 mm.

According to any of the above-described examples of the first embodiment, the registration device 300, 300', 300'' comprises at least one radio-opaque element 301, 301', 301'' arranged in a known geometry with respect to a general geometry of the registration device 300, 300', 300''. Advantageously, the registration device 300, 300', 300'' comprises three radio-opaque elements 301, 301', 301'' formed as beads and arranged in a known geometry with respect to the general geometry of the registration device and with respect to each other. Thanks to those radiopaque elements, this registration device 300, 300', 300" is used to match images of the patient taken before and during surgery, i.e., images taken pre-operatively and per-operatively. For instance, the registration device can be arranged between the tibial and talar trackers, longitudinally. In the present document, the word "longitudinal" refers to a direction parallel, or sensibly parallel to a tibia axis X, for instance illustrated on FIG. 6 which is a rear view of the ankle, making visible part of the tibia Ti, the talus Ta and a calcaneus Ca of said ankle.

Figure 5:
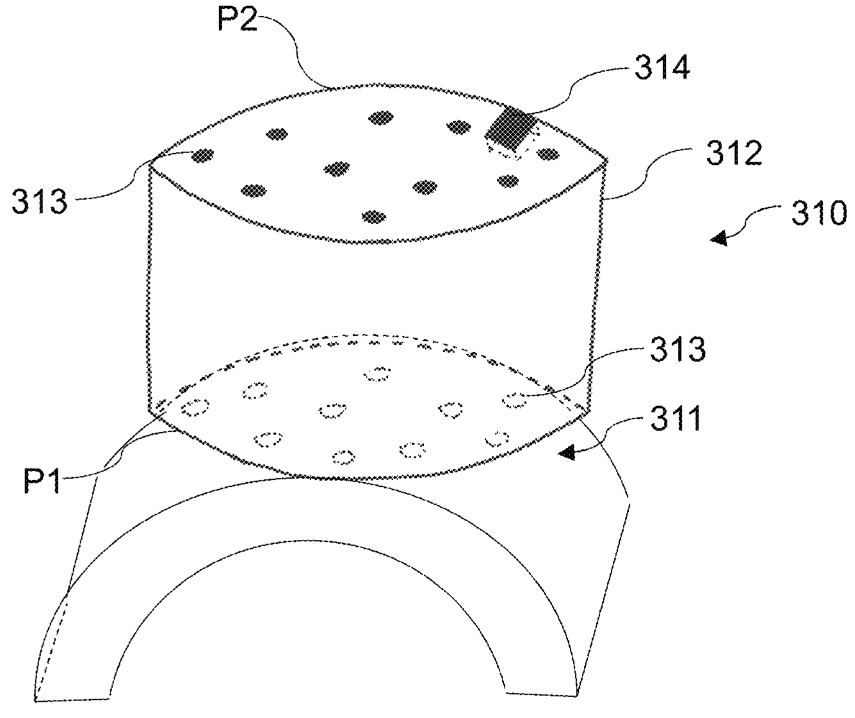
FIG. 5 schematically illustrates a registration device according to a second embodiment.

FIG. 5 illustrates a second embodiment of the registration device 310 which is particularly adapted to be used in a situation where no images are taken pre-operatively. According to this embodiment, the registration device 310 is configured to cover the whole ankle. As illustrated, such a registration device comprises a support 311, here presenting a U-shape, adapted to be placed on the ankle to be treated and supporting a main body 312 of the registration device 310 which comprises at least three radiopaque elements 313 and an electromagnetic transceiver 314. As illustrated, the radiopaque elements 313 are distributed between two distinct planes P1, P2, according to a known geometry. The registration device according to this embodiment is particularly well suited to be used to perform a per-operative registration, as detailed below. Optionally, the registration device comprises an X-ray sensor configured to detect that an X-ray image is taken and to trigger a recording of the pose of the electromagnetic sensors when said X-ray image is taken.

Figure 6:
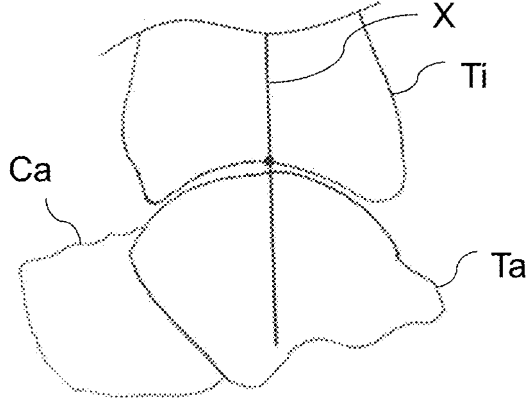
FIG. 6 is a rear view of the ankle to be treated, illustrating a tibial axis of the concerned leg.
Figure 7:
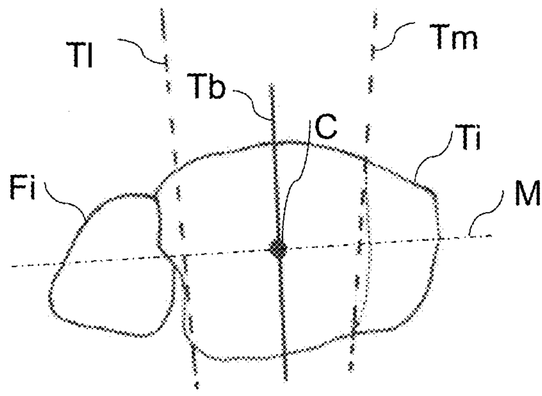
FIG. 7 is a bottom view of the ankle to be treated, illustrating a distal surface of a tibia and of a fibula of the patient's leg.

FIGS. 6 and 7 which are respectively a rear view and a bottom view of the tibia Ti, thus illustrating a distal surface of the tibia Ti and a distal surface of the fibula Fi, further illustrate different anatomical landmarks which can be used to define some morphological criteria used to elaborate a surgical plan of the ankle arthroplasty, amongst which:

- the tibia axis X which is defined as an axis joining a center of the tibial plateau to a center of the distal surface of said tibia,
- a center C of the distal surface of the tibia Ti,
- a tibial bisector Tb defined as the bisector of an angle formed by the crossing of two straight lines Tl, Tm, respectively tangent to the lateral surface of the tibia Ti and to the medial surface of said tibia Ti, and
- a malleolar axis M defined as an axis joining a malleolus of the tibia and a malleolus of the talus.

Other anatomical landmarks—not illustrated here—can also be used, such as:

- a talar bisector defined as the bisector of an angle formed by the crossing of two straight lines respectively tangent to the lateral surface of the talus and to the medial surface of said talus, and
- a medio-lateral distance of the talus, defined as a distance measured between the lateral surface and the medial surface of the talus, perpendicularly to the tibial axis.

The computer-assisted surgery system can also be associated with an imaging device 130. According to the embodiment illustrated on FIG. 1, the computer-assisted surgery system is associated with a cone beam computed tomography device, also referred to as "C-arm". Obviously, this is only an example and the system could be associated with any other known device adapted to acquire 2D or 3D images of a patient. Finally, the computer-assisted surgery system can comprise at least one display 120, for instance arranged on the base of the computer-assisted surgery system. This display 120 can be mounted on an articulated arm 121 so that the user of the system can position it in the most convenient position. Alternatively, the display can be completely separated from the system and mounted on a distinct pole, or it could be attached to the table on which the patient lies. According to yet another alternative, the display could be arranged in an augmented reality device worn by the user.

Figure 8A:
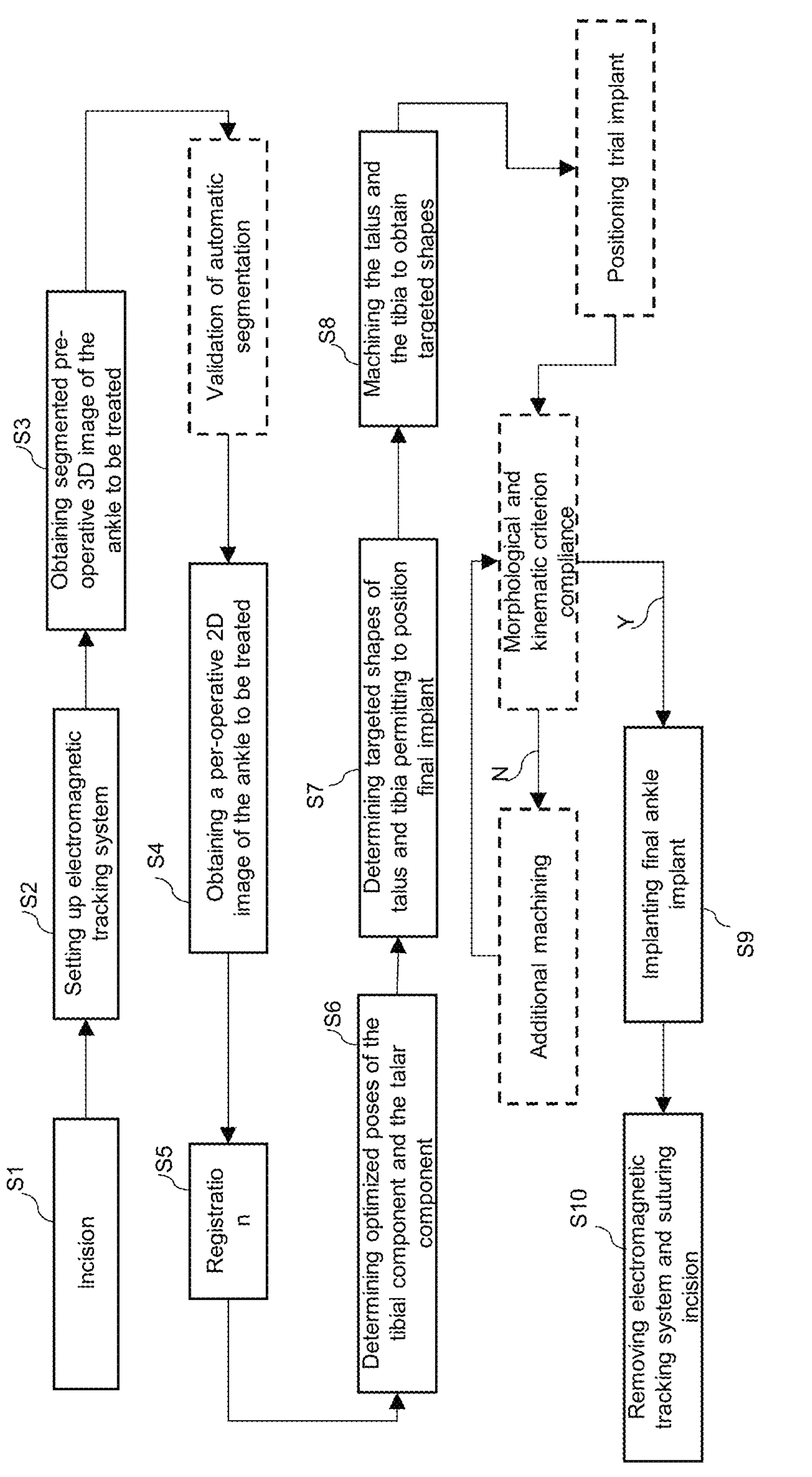
FIGS. 8*a* and 8*b* are schematic representations of the successive steps of the method.

Now referring to FIG. 8*a*, we are going to describe the successive steps to be carried out for performing an ankle arthroplasty according to a first embodiment.

During a first step S1, the user of the system has to make an incision in the patient's skin so that the surgical tool can have access to the ankle's bones, and especially to the tibia and to the talus of the concerned ankle. As evoked, the system comprises the electromagnetic tracking system. A second step S2 thus involves setting up said electromagnetic tracking system by positioning the electromagnetic receivers as well as the electromagnetic transmitter. According to the described embodiment, the talar tracker is attached to the medial surface of the talus, the tibial tracker is attached to the medial surface of the tibia and the surgical tool tracker is attached to the surgical tool, for instance thanks to the extension of the robotic arm described above. The electromagnetic transmitter is also positioned near the receivers. Especially, the electromagnetic transmitter is positioned so that a longest distance measured between the transmitter and any of the bone trackers is below 60 mm, advantageously below 50 mm, as explained above. Optionally, the electromagnetic tracking system could be complemented with inertial sensors, such as accelerometers or gyroscope and/or with an optical tracking system.

A third step S3 comprises obtaining at least one segmented pre-operative 3D image of the ankle to be treated. For instance, the 3D image(s) is acquired pre-operatively, then segmented either manually or automatically and it can then be stored in a storage unit with which the data processor is in communication to obtain said 3D image(s). By "segmented" we here refer to a step during which the different bones displayed on the acquired image are discriminated from each other. Advantageously, the pre-operative 3D image can be acquired while the ankle is in a weight bearing condition, i.e. in a standing position of the patient. Thus, the patient's weight is considered while planning the surgery, which is particularly relevant in an ankle arthroplasty as the ankle supports the weight of the patient.

A fourth step S4 comprises obtaining at least one per-operative 2D image of the ankle to be treated, each per-operative 2D image being acquired while a registration device is placed on the ankle to be treated. Especially, the registration device according to the second embodiment illustrated on FIG. 5 can be used. For instance, each 2D image can be acquired by a known fluoroscopy apparatus.

By "pre-operative", we here refer to any step carried out before the surgery, i.e. before initiating the surgery. For instance, said pre-operative 3D image can be taken a couple of hours or even days before the surgery. By "per-operative", we here refer to something done while the patient is in the operating room.

A fifth step S5 comprises registering the segmented 3D image on the per-operative 2D. This registration permits to match the pre-operative 3D image with the per-operative 2D image so as to display real-time movements of the bones on the 3D model. As mentioned above, the pre-operative 3D image can be segmented manually or automatically. When the segmentation is automatic, it can be done pre-operatively, or it can be done per-operatively. When the 3D image is segmented automatically, the method can comprise an additional step—schematically illustrated with dotted lines—of displaying the segmented 3D image(s), so that the segmentation can be validated and/or adjusted by the user of the system before the fifth step of registration.

To register the segmented 3D image on the per-operative 2D image, the following steps can be implemented, for instance by a processing unit of the computer-assisted surgery system which can be distinct or not from the processing unit described above:

- obtaining at least one 2D projection of each bone from the segmented 3D image,
- determining a transform matrix between the 2D projections of each bone and the per-operative 2D image, for instance based on contour detection,
- determining a transform matrix between the registration device and the electromagnetic tracking system based on measurement of the electromagnetic field emitted or received by the electromagnetic transceiver attached to the registration device,
- determining a transform matrix between the trackers of the electromagnetic tracking system and the segmented 3D image.

Thus, a 3D model of the ankle to be treated is reconstructed using pre-operative 3D image can match the actual displacement applied, in real-time, to said treated ankle.

During a sixth step S6, an optimized pose of the final tibial component with respect to the tibia, and an optimized pose of the final talar component with respect to the tibia are determined, based on at least one morphological criterion. Optionally, these optimized poses can be stored in a storage unit. It is thus understood that when the pre-operative 3D image is taken while the patient is in a weight bearing condition, the optimized poses of the tibial and talar components are also determined particularly for such weight bearing condition, thus improving the comfort of the patient who undergo the described ankle arthroplasty, after said surgery.

The at least one morphological criterion to be considered for planning the surgery is at least one of the following:

- the final tibial component and the final talar component are included in a volume defined by a longitudinal projection of an anterior surface of the tibia bone,
- implant sizes are maximal,
- implant axes are aligned with bone axis.

Figure 11A:
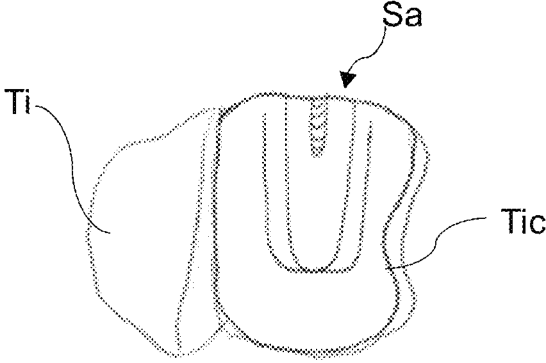
FIGS. 11*a* and 11*b* respectively illustrate a tibial implant implanted on the tibia, viewed on a bottom view and on a side view.
Figure 11B:
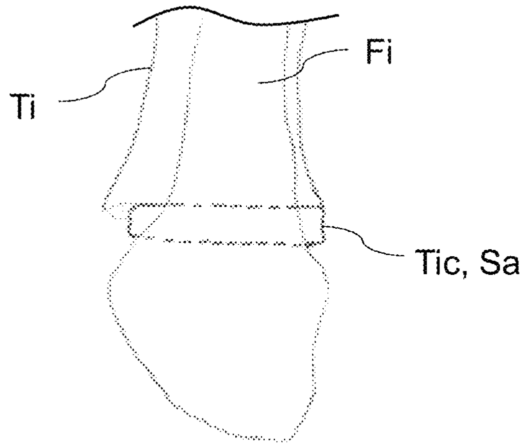

FIGS. 11*a*, 11*b* for instance represent a tibial component which is included in the volume defined by the longitudinal projection of the anterior surface Sa of the tibia Ti. As shown on the bottom view illustrated on FIG. 11*a* and on the side view illustrated on FIG. 11*b*, an edge of the tibial component Tic here perfectly matches the projection of the anterior surface Sa of the tibia.

By "maximal size" of an implant, we here mean that this implant is optimized when it is as big as possible while remaining within contours of the bones on which it is positioned.

The implant axes are defined by the implant designer, and they should match with anatomical landmarks described above. For instance, a main implant axis of the tibial component should match with the tibia axis X, as illustrated on FIG. 6.

Optionally, the step of determining the optimized pose of the final tibial component with respect to the tibia, and the optimized pose of the final talar component with respect to the tibia, can be further based on a set of kinematic data acquired by

- applying defined constraints on the ankle to be treated,
- virtually simulating the applied constraints on the registered 3D image,
- the optimized pose of the final tibial component and of the final talar component being defined to prevent impingement between the final tibial component, the final talar component, the tibia and the talus when the constraints are applied.

The optimized pose of the final tibial component and of the final talar component can also be defined so that a mobility of the treated ankle is at least as wide before and after having implanted the ankle implant, the mobility of the treated ankle being estimated based on at least one of (i) a maximal angle of possible plantar flexion and a maximal angle of possible dorsal flexion of the treated ankle and (ii) a maximal varus/valgus balance. Thus, the constraints applied to the ankle can be a plantar and/or dorsal flexion and/or varus/valgus constraints.

As mentioned above, the acquisition of this set of kinematic data is permitted by the fifth step S5 of registration and by the electromagnetic tracking system.

A seventh step S7 comprises determining a targeted shape of the talus and a targeted shape of the tibia, said targeted shapes being determined so as to permit to position the final tibial component and the final talar component according to their respective planned optimized poses. The targeted shapes of the talus and of the tibia can then be stored as part of a surgical plan to be followed by the user and/or by the computer-assisted surgery system.

Figure 9:
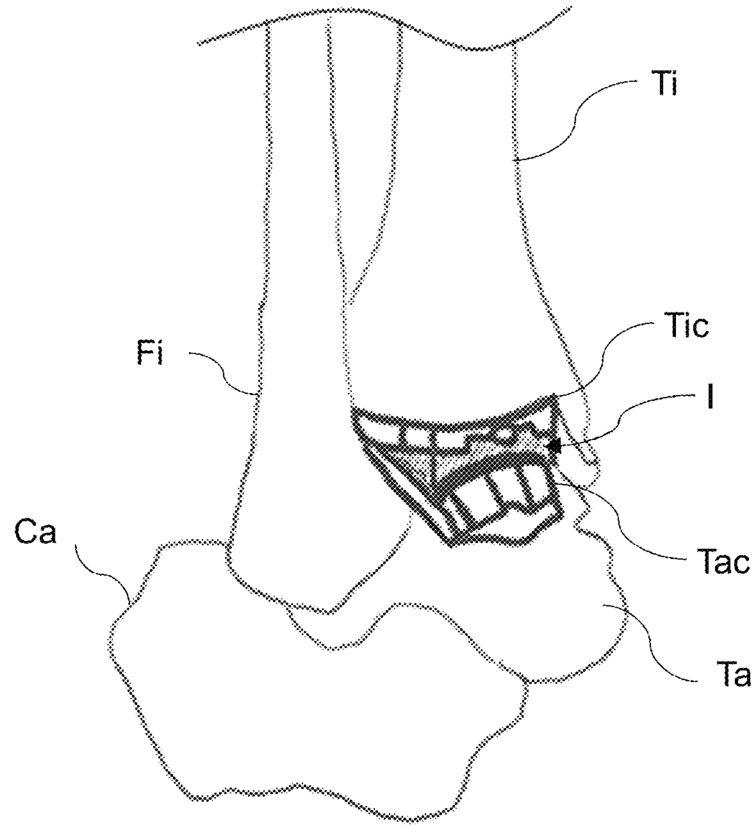
FIG. 9 schematically illustrates an ankle on which a final implant has been fixed.

An eight step S8 comprises machining the talus and the tibia with the surgical tool held by the robotic arm to obtain the targeted shapes. As for instance illustrated on FIG. 9, the final implant comprises the final talar component Tac, the final tibial component Tic and the final insert I positioned between the talar component Tac and the tibial component Tic and adapted to allow movements of both components with respect to each other and with respect to the insert I. For instance, this insert can be made of polyethylene.

As it is used for machining bones, the surgical tool is here formed as a cutting tool, such as a saw or a burr, for instance. As mentioned above, the surgical tool can, for instance, be guided by the user, through the input device of the system. Alternatively, the computer-assisted surgery system can be adapted to machine the bones automatically, based on the planning and on the determined poses of the concerned bones obtained thanks to the tracking system.

Referring back to FIG. 8*a*, a ninth step S9 comprises implanting the final tibial component on the machined tibia, the final talar component on the machined talus, and the final insert of the ankle implant between the final tibial component and the final talar component.

The tenth steps S10 then comprises removing the tracking system and suturing the at least one incision previously made.

Figure 8B:
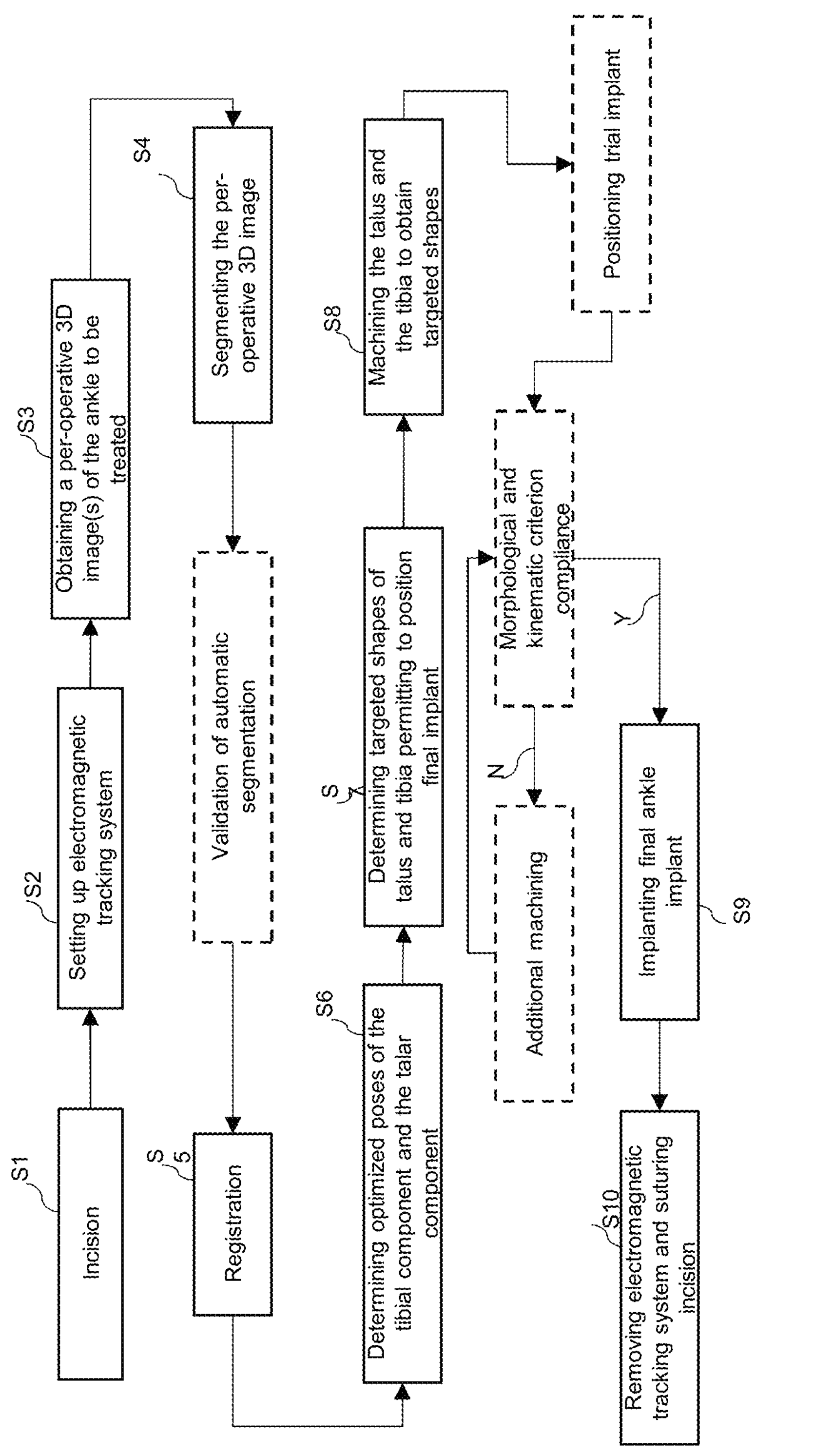

FIG. 8*b* illustrates schematically the method according to a second embodiment. The method according to the second embodiment differs from the method according to the first embodiment concerning the third and fourth steps S3 and S4. As illustrated, according to this second embodiment, only per-operatively acquired images of the ankle to be treated are taken. Particularly, the third step S3 comprises obtaining a 3D image taken per-operatively while the registration device according to the first embodiment described above with reference to FIG. 4 is placed on the ankle. The obtained 3D image is then segmented (step S4) to discriminate each bone from one another and then the segmented 3D image is registered, so as to display real-time movements of the ankle.

To perform such a per-operative registration, the following steps can be implemented, for instance by a processing unit of the computer-assisted surgery system which can be distinct or not from the processing unit described above:

determining a first transform matrix, for each segmented bone, between the 3D image and the corresponding bone tracker, based on the known geometry of the radiopaque elements of the registration device and on a known geometry of each bone tracker with respect to the concerned tracked bone, determining a second transform matrix between the registration device and the electromagnetic tracking system based on measurement of the electromagnetic field emitted or received by the electromagnetic transceiver attached to the registration device, determining a final transform matrix between the per-operative 3D image and the electromagnetic tracking system based on the determined first and second transform matrices and on a known transform matrix between the electromagnetic transceiver of the registration device and the radiopaque elements of the registration device.

The determination of the optimized poses of the talar component and of the tibial component is realized based on the segmented image. To take into account the weight of the patient, as in the first embodiment, it is advantageous to be able to mimic the weight bearing condition while the patient is lying on the surgical table.

Figure 10:
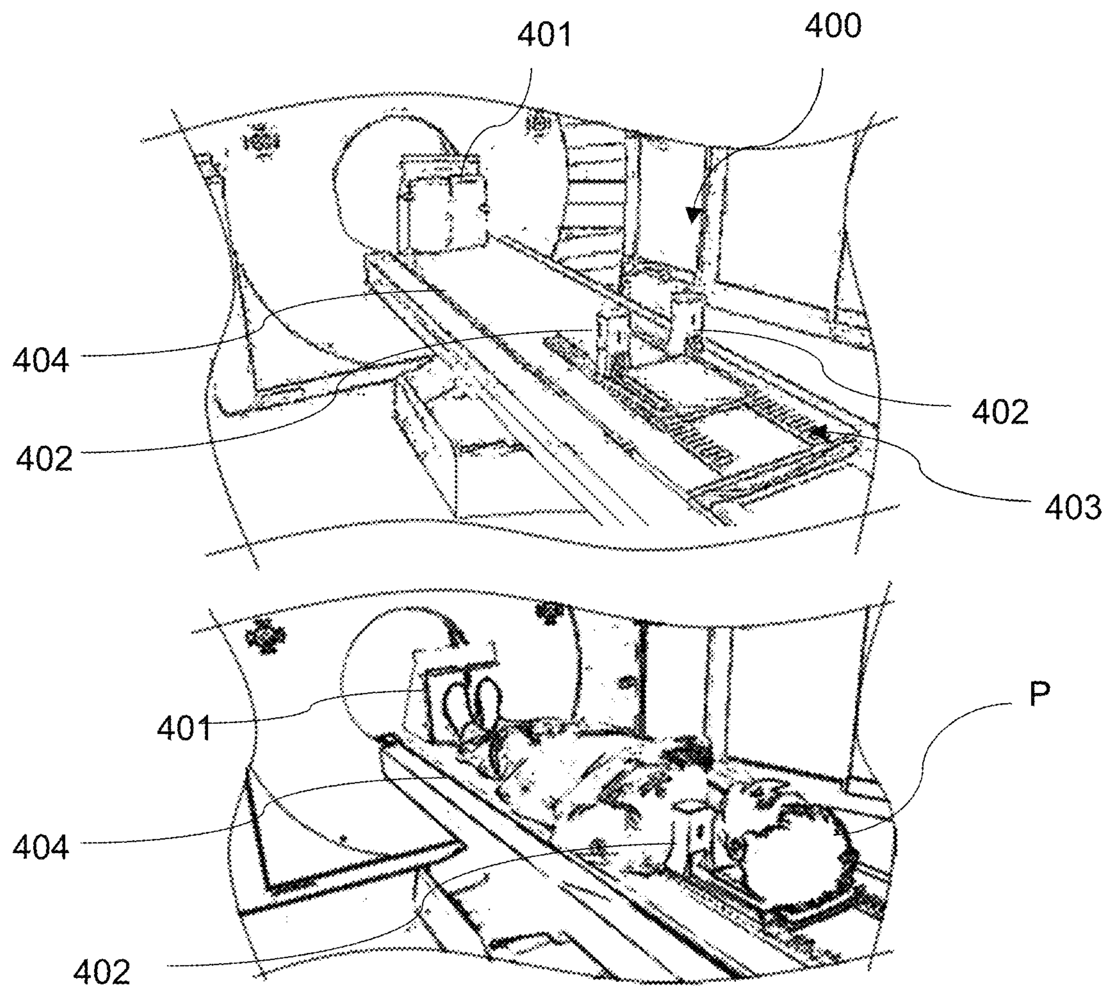
FIG. 10 is a perspective view of a device adapted to mimic a weight bearing position on a lying patient.

Reproducing weight bearing condition can for instance be done thanks to a device 400 illustrated on FIG. 10. As shown, such device 400 comprises a plate 401 and at least one maintaining element 402, the plate 401 being adapted to be positioned against at least the foot of the leg to be treated, advantageously both feet of the patient, while the maintaining element 402 is adapted to be positioned against the shoulders of the patient P. Advantageously, the device 400 comprises two maintaining elements 402, for instance formed as cushions, respectively adapted to be positioned against one of the shoulders of the patient P. The maintaining elements 402 are also attached, with a notched system 403, to a board 404 on which the patient lies. Thus, by applying a mechanical pressure on the ankle of the patient, the device 400 permits to mimic a weight-bearing position, and thus permits to acquire the needed 2D image(s), per-operatively, and without moving the patient P. Particularly, the mechanical pressure is applied by displacing at least one of the plate 401 and the maintaining elements 402. According to different embodiments, the mechanical pressure can be applied manually by an operator, or the device 400 can be equipped with motors configured to displace the plate and/or the maintaining elements to apply the mechanical pressure automatically.

The level of mechanical pressure to be applied on the patient's ankle is directly related to his/her weight. Advantageously, the mechanical pressure is applied along a direction perpendicular to the plate on which the patient's foot is leaning and which crosses a hip center of the leg to be treated. Such hip center can be found thanks to any known method, such as a pivot method, or by palpation for instance. Optionally, the device 400 can comprise a laser source adapted to emit a laser beam propagating parallel to the direction along which the pressure should be applied in order to indicate to the user of the system said direction.

As schematically illustrated with dotted lines on FIGS. **8*a* and 8*b***, either embodiment could comprise additional optional steps of positioning a trial implant on the prepared ankle, before positioning the final implant. Advantageously, this optional step is followed by a step of verifying that the pose of the trial implant complies with the defined morphological criterion. To check this compliance of the morphological criterion, the user can for instance acquire at least one 2D image of the ankle with the implanted trial implant.

If the pose of the trial implant complies with the morphological criterion, then such trial implant can be replaced by the final implant as described with reference to step S9. If the pose of the trial implant does not comply with the morphological criterion, then the system can be configured to determine additional cuts needed so that such trial implant complies with the defined morphological criterion. These steps can obviously be repeated as many times as needed before implanting the final implant.

The invention claimed is:

1. A method for performing an ankle arthroplasty on a patient's leg by implanting a final ankle implant comprising at least one final tibial component, at least one final talar component and at least one final insert movable with respect to the final tibial component and to the final talar component, using a computer-assisted surgery system comprising a robotic arm holding a surgical tool and an electromagnetic tracking system comprising at least a talar tracker, a tibial tracker and at least one surgical tool tracker, the method comprising:

fixing the talar tracker, the tibial tracker and the surgical tool tracker, respectively, to a talus of the patient's leg, to a tibia of the patient's leg and to the surgical tool, according to known geometries, to determine relative poses of the talus, the tibia and the surgical tool with respect to one another, obtaining at least one segmented pre-operative 3D image of the ankle, obtaining at least one per-operative 2D image of the ankle, each per-operative 2D image being acquired while a registration device comprising at least three radiopaque elements and at least one electromagnetic transceiver is placed on the ankle, registering the segmented pre-operative 3D image on each per-operative 2D image, using the registration device, determining an optimized pose of the final tibial component with respect to the tibia, and an optimized pose of the final talar component with respect to the tibia, based on at least one morphological criterion, determining a targeted shape of the talus and a targeted shape of the tibia to permit to position the final tibial component and the final talar component according to their respective planned optimized poses, machining the talus and the tibia with the surgical tool held by the robotic arm to obtain the targeted shapes, and implanting the final tibial component on the machined tibia, the final talar component on the machined talus, and the final insert of the ankle implant between the final tibial component and the final talar component.

2. The method according to claim 1, further comprising, before implanting the final tibial component, the final talar component and the final insert:

implanting a trial ankle implant by implanting a trial tibial component on the machined tibia, a trial talar component on the machined talus, and a trial insert between the trial tibial component and the trial talar component, checking if a pose of each trial component complies with the at least one morphological criterion, and removing the trial ankle implant.

3. The method according to claim 2, further comprising:

determining that additional machining of at least one of the talus and the tibia is needed if the pose of at least one trial component does not comply with the at least one morphological criterion, planning and performing said additional machining with the surgical tool, and implanting the final ankle implant.

4. The method according to claim 1, further comprising checking if the pose of each final component complies with the at least one morphological criterion.

5. The method according to claim 1, wherein the morphological criterion comprises at least one of the following:

the final tibial component and the final talar component are included in a volume defined by a longitudinal projection of an anterior surface of the tibia bone, implant sizes are maximal, implant axes are aligned with bone axes, and a gap between the tibia and the talus components of the implant is at least as high than a width of the final insert.

6. The method according to claim 1, wherein the electromagnetic tracking system comprises at least one data processor and an electromagnetic transmitter adapted to emit an electromagnetic field, each of the tibial tracker, the talar tracker and the surgical tool tracker being an electromagnetic receiver adapted to receive and measure the electromagnetic field, the data processor being adapted to determine a relative pose of the talus, the tibia and the surgical tool, based on the electromagnetic field measured by each electromagnetic receiver and on the known geometric relation between the tibial tracker and the tibia, the talar tracker and the tibia and the surgical tool tracker and the surgical tool.

7. The method according to claim 6, wherein the talar tracker is fixed to a medial surface of the talus.

8. The method according to claim 6, wherein the electromagnetic transmitter is positioned medially with respect to the tibial and talar trackers.

9. The method according to claim 6, wherein the surgical tool tracker is rigidly fixed to an extension of the robotic arm, the extension being configured to position the surgical tool tracker medially with respect to the electromagnetic transmitter and to the tibial and talar trackers.

10. The method according to claim 1, wherein each pre-operative 3D image is acquired while the patient is in a weight bearing position.

11. The method according to claim 1, wherein determining the optimized pose of the final tibial component with respect to the tibia and the optimized pose of the final talar component with respect to the tibia is further based on a set of kinematic data acquired by applying defined constraints on the ankle to be treated, and virtually simulating the applied constraints on the registered 3D image, the optimized pose of the final tibial component and of the final talar component being defined to prevent impingement between the final tibial component, the final talar component, the tibia and the talus when the constraints are applied.

12. The method of claim 11, wherein the optimized pose of the final tibial component and of the final talar component are defined so that a mobility of the treated ankle is at least as wide before and after implantation of the ankle implant, the mobility of the treated ankle being estimated based on at least one of (i) a maximal angle of possible plantar flexion and a maximal angle of possible dorsal flexion of the treated ankle and (ii) a maximal varus/valgus balance.

13. A method for performing an ankle arthroplasty on a patient's leg by implanting a final ankle implant comprising at least one final tibial component, at least one final talar component and at least one final insert movable with respect to the final tibial component and to the final talar component, using a computer-assisted surgery system comprising a robotic arm holding a surgical tool and, an electromagnetic tracking system comprising at least a talar tracker, a tibial tracker and at least one surgical tool tracker, the method comprising:

fixing the talar tracker, the tibial tracker and the surgical tool tracker, respectively, to a talus of the patient's leg, to a tibia of the patient's leg and to the surgical tool, to determine relative poses of the talus, the tibia and the surgical tool with respect to one another, obtaining at least one per-operative 3D image of the ankle while a registration device comprising at least three radiopaque elements and at least one electromagnetic transceiver is placed on the ankle, the 3D image being acquired for a given position of the talus with respect to the tibia, segmenting the per-operative 3D image of the ankle, recording an optimized pose of the final tibial component with respect to the tibia, and an optimized pose of the final talar component with respect to the tibia, based on at least one morphological criterion, determining a targeted shape of the talus and a targeted shape of the tibia to permit to position the final tibial component and the final talar component according to their respective planned optimized poses, machining the talus and the tibia with the surgical tool held by the robotic arm to obtain the targeted shapes, and implanting the final tibial component on the machined tibia, the final talar component on the machined talus, and the final insert of the ankle implant between the final tibial component and the final talar component.

14. The method according to claim 13, wherein the given position of the talus with respect to the tibia corresponds to a weight bearing position of the patient, and wherein obtaining the per-operative 3D image of the ankle comprises:

positioning the patient on a board in a lying position, feet soles of the patient being positioned against a plate perpendicular to the board, determining a hip center of the patient's leg, applying a mechanical pressure on the ankle, along a direction perpendicular to the plate and passing through the hip center, to simulate a weight bearing condition, and recording the relative poses of the tibia and the talus with respect to one another in the simulated weight bearing position of the patient.

15. The method according to claim 14, wherein the relative poses of the tibia and the talus with respect to one another in the simulated weight bearing position of the patient are recorded based on positional data obtained by the electromagnetic tracking system.

16. The method according to claim 14, wherein the board comprises at least one laser source adapted to emit a laser beam, the method further comprising:

orienting the laser source to propagate the laser beam perpendicularly to the plate and toward the hip center, the direction of the application of the mechanical pressure being materialized by said laser beam.

17. The method according to claim 14, wherein the mechanical pressure depends on at least a weight of the patient.

18. The method according to claim 14, wherein the mechanical pressure is modified by displacing, manually or automatically, the plate.

19. The method according to claim 13, wherein determining the optimized pose of the final tibial component with respect to the tibia and the optimized pose of the final talar component with respect to the tibia is further based on a set of kinematic data acquired by applying defined constraints on the ankle to be treated, and virtually simulating the applied constraints on the registered 3D image, the optimized pose of the final tibial component and of the final talar component being defined to prevent impingement between the final tibial component, the final talar component, the tibia and the talus when the constraints are applied.

20. The method of claim 18, wherein the optimized pose of the final tibial component and of the final talar component are defined so that a mobility of the treated ankle is at least as wide before and after implantation of the ankle implant, the mobility of the treated ankle being estimated based on at least one of (i) a maximal angle of possible plantar flexion and a maximal angle of possible dorsal flexion of the treated ankle and (ii) a maximal varus/valgus balance.

* * * * *